| (12) | United States Patent | (10) Patent No.: | US 9,060,819 B2 |
|---|---|---|---|
| | Richards et al. | (45) Date of Patent: | Jun. 23, 2015 |

(54) BONE FIXATION DEVICE WITH COVER

(75) Inventors: Robert Geoffrey Richards, Davos Dorf (CH); Christoph Martin Noetzli, Zurich (CH)

(73) Assignee: AO TECHNOLOGY AG, Chur (CH)

( * ) Notice: Subject to any disclaimer, the term of this patent is extended or adjusted under 35 U.S.C. 154(b) by 273 days.

(21) Appl. No.: 13/000,988

(22) PCT Filed: Mar. 17, 2009

(86) PCT No.: PCT/CH2009/000095
§ 371 (c)(1),
(2), (4) Date: Feb. 2, 2011

(87) PCT Pub. No.: WO2009/155715
PCT Pub. Date: Dec. 30, 2009

(65) Prior Publication Data
US 2011/0172667 A1 Jul. 14, 2011

(30) Foreign Application Priority Data

Jun. 26, 2008 (WO) ................ PCT/CH2008/000290

(51) Int. Cl.
*A61B 17/72* (2006.01)
*A61B 17/80* (2006.01)

(52) U.S. Cl.
CPC ............. *A61B 17/72* (2013.01); *A61B 17/7233* (2013.01); *A61B 17/7258* (2013.01); *A61B 17/80* (2013.01); *A61B 17/8042* (2013.01)

(58) Field of Classification Search
USPC ..................... 606/62–68, 280–299
See application file for complete search history.

(56) References Cited

U.S. PATENT DOCUMENTS

| 5,304,121 | A | * | 4/1994 | Sahatjian | ........................ 604/509 |
| 5,534,027 | A | * | 7/1996 | Hodorek | ........................ 128/898 |

(Continued)

FOREIGN PATENT DOCUMENTS

WO      2007/082004 A2      7/2007

OTHER PUBLICATIONS

Steven Kurtz, UHMWPE Biomaterials Handbook: Ultra High Molecular Weight Polyethylene in Total Joint Replacement and Medical Devices. Academic Press, Apr. 27, 2009, p. 524 accessed Dec. 9, 2014.*

*Primary Examiner* — Jan Christopher Merene
*Assistant Examiner* — Steven Cotroneo
(74) *Attorney, Agent, or Firm* — Rankin, Hill & Clark LLP

(57) ABSTRACT

A bone fixation device (1) comprising: A) a first bone implant (2) with at least one through hole (11) having an upper opening (3) with the area A and a lower opening (4) in the case of a bone plate (10) as the first bone implant (2); or an outer opening with the area A and an inner opening in the case of a hollow intramedullary nail as the first bone implant (2); B) at least one second bone implant (5) with a head (6) and a shaft for insertion into one or more of said through holes (11); and C) at least one closing cover (7) for closing said upper opening (3) or outer opening of said through hole (11) for preventing bone and soft tissue ingrowth and/or bacterial invasion into said through hole (11) and into said second bone implant (5) wherein said closing cover (7) is D) removably attachable to said first bone implant (2); and E) dimensioned and shaped in such a way that upon attachment to said first bone implant (2) it is apt to cover at least the entire area A of said upper opening (3) or outer opening and of any of said second bone implants (5) if inserted into said through hole (11).

28 Claims, 3 Drawing Sheets

(56) References Cited

U.S. PATENT DOCUMENTS

| | | | |
|---|---|---|---|
| 5,935,127 A * | 8/1999 | Border | 606/62 |
| 6,022,350 A * | 2/2000 | Ganem | 606/272 |
| 6,235,034 B1 * | 5/2001 | Bray | 606/71 |
| 6,406,478 B1 * | 6/2002 | Kuo | 606/71 |
| 7,094,239 B1 * | 8/2006 | Michelson | 606/70 |
| 7,833,254 B2 * | 11/2010 | Celli et al. | 606/295 |
| 2002/0071902 A1 * | 6/2002 | Ding et al. | 427/2.24 |
| 2002/0103488 A1 * | 8/2002 | Lower et al. | 606/62 |
| 2002/0151898 A1 | 10/2002 | Sohngen et al. | |
| 2002/0173792 A1 * | 11/2002 | Severns et al. | 606/62 |
| 2007/0288016 A1 | 12/2007 | Halder | |
| 2008/0177330 A1 * | 7/2008 | Ralph et al. | 606/290 |

\* cited by examiner

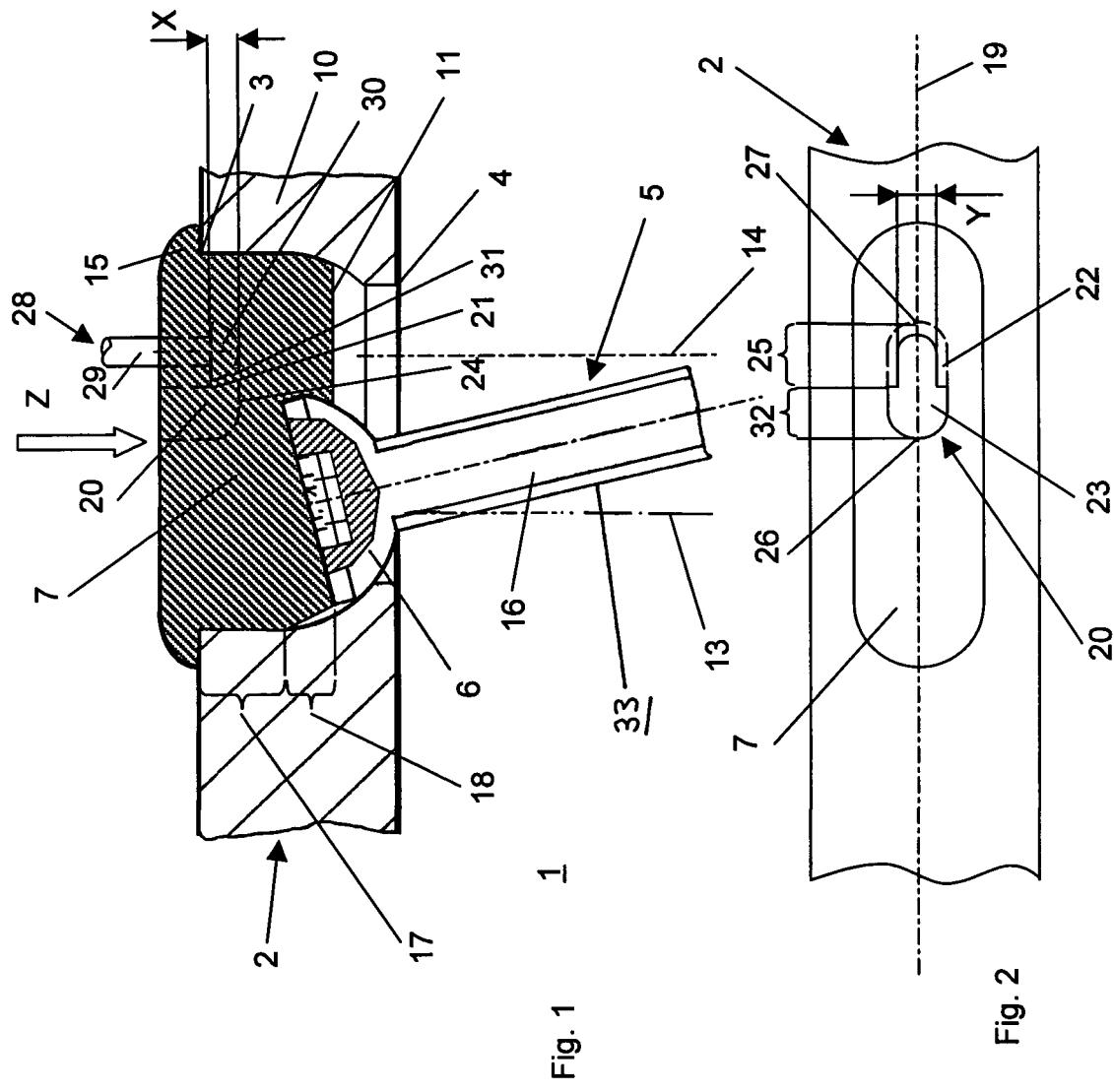

BONE FIXATION DEVICE WITH COVER

FIELD OF THE INVENTION

The invention relates to a bone fixation device with a cover for closing an upper opening or an outer opening of a through hole provided in a first bone implant to prevent bone and soft tissue ingrowth and/or bacterial invasion into said through hole, to a kit for bone fixation including such a bone fixation device and a gel and a kit for bone fixation including such a bone fixation device and an insertion instrument.

DESCRIPTION OF THE PRIOR ART

U.S. Pat. No. 5,935,127 BORDER discloses a bone plate with long through holes where resorbable inserts are placed. These inserts are pre-operatively inserted into the longitudinal through holes and attached thereto. After the bone plate has been positioned in order to span a fracture bores are drilled in a surgeon desired position through the inserts and then fasteners are advanced through said drilled bores such that the threaded shafts of the fasteners are screwed into the bone.

US 2002/0173792 SEVERNS ET AL. shows an intramedullary nail with a distal through hole with a spacer preferably made of a bioresorbable material. The spacer is positioned within the through hole. To support the intramedullary nail a bone fastener such as a bone screw is advanced through the spacer in the through hole and through the bone. Before insertion of the bone screw a respective bore is drilled through the spacer in a surgeon desired position.

A disadvantage of these known devices is that these inserts would not be suitable to avoid ingrowth of tissue since the inserts do not cover the entire areas of the upper openings or outer openings of the through holes in the bone implant.

SUMMARY OF THE INVENTION

It is an object of the invention to provide a bone fixation device including means which prevent soft and hard tissue as well as bacteria from growing into apertures, slits between two separate parts of the bone fixation device and into through holes being provided in at least one of the parts of the bone fixation device.

The bone fixation device according to the present invention solves the posed problem with a bone fixation device with a cover for closing an upper opening or an outer opening of a through hole provided in a first bone implant to prevent bone and soft tissue ingrowth and/or bacterial invasion into said through hole, a kit for bone fixation that includes such a bone fixation device and a gel and a kit for bone fixation that includes such a bone fixation device and an insertion instrument.

The device according to the present invention allows the following advantages:
- the cover which is put into through holes within the implant prevents bone or connective soft tissues from growing into these spaces;
- bone/soft tissue ingrowth and concomitantly bacteria population filling the dead spaces in the implant fixation element interface or empty through holes can be prevented;
- facilitating removal of the bone fixation device since bone / soft tissue ingrowth leads not only to additional, and highly time consuming procedures, but also introduces a high risk of re-fracturing the bone or damaging the implant fixation element interface which as such could lead to breakage of the fixation element causing again additional procedures;
- the cover can be placed in all through holes before the implant is used and can be popped out of the through holes used for fixation following which the element (e.g. screw) is inserted and then an alternate cover can be fitted to correspond to the changed shape of the through hole with the fixation element (e.g. screw) inside; and
- the cover can be placed into the implant (e.g. intramedullary nail or bone plate) during the packaging process so the implant with the cover is packed sterile for immediate use.

In another embodiment the bone fixation device does not include a second bone implant. Such the bone fixation device may comprise one or two the closing covers which can be used to cover the front and/or rear opening of the cannulation of e.g. a cannulated intramedullary nail or a cannulated bone screw. Such cannulation usually runs completely through the device and can be used for placement of the device in the correct position within the bone with the use of a guide wire, which is removed after placement of the bone fixation device. After removal of the guide wire the openings at the front and/or rear end of the device can be covered by said closing cover.

In a further embodiment said at least one closing cover is suitable for closing said upper opening or outer opening of said through hole for preventing bone and soft tissue ingrowth and/or bacterial invasion into said second bone implant.

In yet a further embodiment said first bone implant is a bone plate having at least one elongated through hole.

In another embodiment said elongated through hole of said bone plate has multiple fixation possibilities, said through hole preferably comprises a first section with a concavely rounded recess suitable for receiving a hemispherical head of a bone screw and at the side of said first section a second section with a conical interior thread for engagement with a complementary conical locking screw head of a bone screw.

In still another embodiment said first bone implant is an intramedullary nail with a longitudinal axis and a cavity extending parallel to said longitudinal axis and wherein. said at least one through hole penetrates said intramedullary nail transverse to said longitudinal axis and in the range of said cavity, said at least one through hole forming two outer openings at the peripheral surface of the intramedullary nail and two inner openings towards said cavity.

In a further embodiment said second bone implant is a bone screw.

In yet a further embodiment said intramedullary nail comprises a rear end and a front end and wherein said cavity extends through said intramedullary nail from said rear end to said front end such forming a front opening and a rear opening. The second implant can be a locking screw or e.g. a locking blade inserted in the transverse opening at the rear end of the intramedullary nail In another embodiment said bone fixation device additionally comprises at least one front cover for closing said lower opening of at least one through hole in the case of a bone plate as the first bone implant. This second (lower) cover in the case of a bone plate can be fixed to the wall of the through hole e.g. by means of an adhesive, press fit or form fit (lip/groove).

In yet a further embodiment said bone fixation device additionally comprises a front cover for closing said front opening of said cavity in the case of an intramedullary nail as the first bone implant. The second (lower) cover in the case of an intramedullary nail can be fixed to the intramedullary nail, e.g. by elastically compressing the front cover during insertion such that a first portion is fixed in the cavity by means of a press fit and an elastic expansion forming a shoulder which results on a second portion which protrudes over the front end of the intramedullary nail.

In another embodiment said bone fixation device additionally comprises an end cover for closing said rear opening of said cavity in the case of an intramedullary nail as the first bone implant.

In a further embodiment said front cover and/or end cover has a trailing end which is provided with a pocket hole for receiving an insertion instrument. The pocket hole is used as an instrument receiving opening and can be provided with an interior thread or with a bayonet-type locking means, such that said insertion instrument can be reversibly attached to the cover.

In another embodiment said closing cover and/or front cover and/or end cover is made of an elastic material. This configuration allows the advantage that the front cover can such be pushed e.g. through the cannula of an intramedullary nail from the rear end of the nail so far that a portion of the cover protrudes over the front end resulting in an expansion of the latter portion (retrofit). The cover could be removably attached to the tip of a guide wire such that when removing the guide wire the cover becomes trapped at the front opening of the cannula, detaches from the guide wire and seals the front opening of the cannulation of the intramedullary nail.

In yet another embodiment said closing cover and/or front cover and/or end cover comprises a material with a contact angle smaller than 60°, preferably smaller than 30°.

In still a further embodiment said material is a hydrophilic material such allowing the advantage that said extreme hydrophilic materials prevent adhesion of bacteria to the implant cover and minimize soft and hard tissue adhesion. The surface is too wet for such interactions.

In another embodiment said closing cover and/or front cover and/or end cover comprises a material with a contact angle larger than 80°, preferably larger than 100°.

In a further embodiment said material is a hydrophobic material. This allows the advantage that said hydrophobic materials prevent adhesion of bacteria to the implant cover and minimize soft and hard tissue adhesion. The contact interface on such a surface is too small to allow protein adsorption and ensuing tissue and/or bacterial adhesion.

In still a further embodiment said material is degradable such as, but not limited to Poly-(ε-caprolactone) or a PLGA polymer such as Poly(L-lactic acid-co-glycol acid).

In yet a further embodiment said material is non-degradable, such as, but not limited to Poly(arlyetherkeytones) including examples such as, but not limited to PEEK (poly (ether ether ketone), PEKK (poly(ether ketone ketone) or PEK poly(ether ketone).

In another embodiment said material is a composite of said degradable material and another material examples such as, but not limited to Beta-tricalcium phosphate (β-TCP) or Hydroxyapatite (HA) or carbon.

In a further embodiment said material is a composite of said non-degradable material and another material examples such as but not limited to Beta-tricalcium phosphate (β-TCP) or Hydroxyapatite (HA) or carbon.

In another embodiment said closing cover is dimensioned and shaped in such a way that upon attachment to said bone implant it is apt to cover more than said area A to prevent tissue and bacteria ingrowth of said upper opening or outer opening, preferably 25% more than A.

In still a further embodiment the geometry of at least a central portion of the said closing cover and/or front cover and/or end cover is adapted to the shape of the through hole.

In yet a further embodiment the geometry of the lower side of the said closing cover is adapted to the shape of said head of said second bone implant.

In another embodiment said closing cover is dimensioned and shaped in such a way that upon attachment to said first bone implant it is apt to cover more than one of said through holes.

The front cover and/or end cover can further comprise a removal hole for insertion of a removing instrument. Said removal hole comprises axial retaining means for said removing instrument, e.g. in the form of a bayonet catch or an internal thread.

In a further embodiment said removal hole is formed as an elongated recess with its long axis parallel to the longitudinal axis of the first bone implant.

In another embodiment said elongated recess comprises a restriction which forms an undercut with a shoulder such forming a hold for an e.g. semispherical tip of a removing instrument when pulling out the cover from said through hole in said first bone implant. A second section of the elongated recess the opening of the elongated recess is not restricted such allowing the shaft of the removing instrument to pass therethrough. The removing instrument can such be inserted into the removal hole in the second section of the elongated hole and displaced into the first section for removal of the cover.

The kit for bone fixation including a bone fixation device and a gel has the particular advantage that the combination of a mechanically resistant cover with a semifluid material (gel) allows the gel to fill the micro spaces very efficiently and other areas where it is difficult to reach the space through the opening with the mechanically resistant cover.

In a further embodiment of such kit said gel is a highly hydrated polymeric material with a water content >30% by weight. Such said gel is particularly suitable for a use of the gel for filling the cavity of said nail with said gel. Suitable materials for such gel are disclosed in Park J B, Lakes R S. Biomaterials: an introduction, 2nd ed. New York: Plenum Press; 1992.

In yet a further embodiment said gel is based on a polymer with hydrophilic chains of synthetic origin.

In another embodiment said gel is based on a polymer with hydrophilic chains of natural origin.

In yet another embodiment said gel is an injectable solution apt to gel in-situ.

The above hydrogels are generally based on hydrophilic polymer chains, which are either synthetic or natural in origin. The structural integrity of hydrogels depends on cross-links formed between polymer chains via various chemical bonds and physical interactions. Suitable hydrogels can be degradable or non-degradable depending of the chemistry and molecular weight of the polymer chains and the crosslinks. They can be injectable solutions that gel in situ by reactive chemical groups (i.e. isocyanate, carbodiimide), UV irradiation, heating, by blending with other polymers (i.e. poly(glycolic acid), polylactic-co-glycolic acid), chitosan).

Synthetic hydrogel materials include poly(ethylene oxide) (PEO), poly(vinyl alcohol) (PVA), poly(acrylic acid) (PAA), poly(propylene furmarate-co-ethylene glycol) (P(PF-co-EG)), poly(urethane)s and polypeptides. Block copolymers of PEO and poly(l-lactic acid) (PLLA) and poly(ethylene glycol) and poly(-caprolactone) can also be used.

Natural derived hydrogel polymers include agarose, alginate, chitosan, collagen, fibrin, gelatin, and hyaluronic acid.

The kit for bone fixation can include insertion instrument reversibly attachable to said front cover and/or end cover. Further, said insertion instrument can comprise securing means reversibly fastenable to said pocket hole in order to insert the front cover through the cavity of said intramedullary nail from the rear end to the front end.

A BRIEF DESCRIPTION OF THE DRAWINGS

One embodiment of the invention will be described in the following by way of example and with reference to the accompanying drawings in which:

FIG. 1 illustrates a longitudinal section through one embodiment of the bone fixation device according to the invention;

FIG. 2 illustrates a top view on the bone fixation device of FIG. 1;

Figure 3:
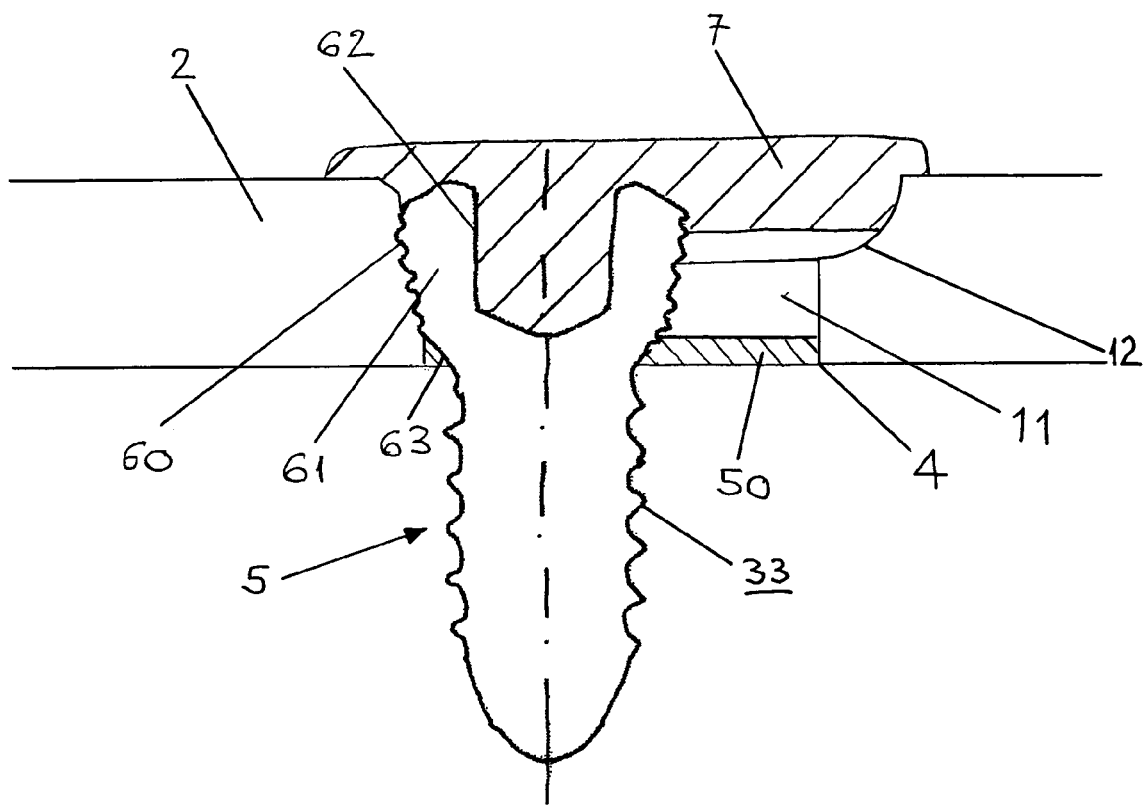
FIG. 3 illustrates a longitudinal section through another embodiment of the bone fixation device according to the invention.

FIGS. 1 and 2 illustrate an embodiment of the bone fixation device 1 comprising a first bone implant 2 which is configured as a bone plate 10 and second bone implants 5 which are configured as bone screws. In FIG. 1 only a portion of the bone plate 10 viewed in a longitudinal cross section is shown. Said bone plate 10 as well as said bone screws are commercially available implants (e.g. SYNTHES@ standard implants). The elongated through holes 11 are provided with an upper opening 3 with the area A viewed in the direction of arrow Z and a lower opening 4, whereby the transition between the upper opening 3 and the lower opening 4 is rounded such that the hemispherical head 6 of said bone screw can be seated in a manner allowing to pivot said bone screw with respect of the axes 13, 14 of the terminal circular portions of said elongated through hole 11. Said elongated through holes 11 additionally allow to provide multiple fixation possibilities in the longitudinal direction of said bone plate 10. Further, said bone screws comprise a shaft 16 with an external thread to be anchored in a bone. For each elongated through hole 11 a closing cover 7 is provided which is suitable for closing said upper opening 3 of said through hole 11 to prevent bone and soft tissue ingrowth and/or bacterial invasion into said through hole 11 and into said bone screw. The geometry of a central portion 17 of said closing cover 7 is adapted to the shape of said through hole 11, here in particular to said upper opening 3. Said closing cover 7 is removably attachable to said bone plate 10 by means of a press-fit between the peripheral wall of said central portion 17 of said closing cover 7 and the wall of said upper opening 3. Further, said closing cover 7 is dimensioned and shaped in such a way that upon attachment to said bone plate 10 it is apt to cover about 25% more than the entire area A of said upper opening 3 by means of an enlarged rear portion 15 of said closing cover 7. By means of said closing cover 7 the recess for a driving means arranged in said head 6 of said bone screw inserted into said through hole 11 is covered as well due to an elastically deformable front portion 18 of said closing cover 7.

The closing cover 7 further comprises a removal hole 20 for insertion of a removing instrument 28. Said removal hole 20 is formed as a elongated recess 23 with its long axis parallel to the longitudinal axis 19 of the first bone implant 2. The bottom 24 of the elongated recess 23 semi-circularly curved in a cross-section orthogonal to the longitudinal axis 19 of the first bone implant 2 and curved with the same radius at the first and second ends 26, 27 which limit the length of the elongated recess 19 in the direction parallel to the longitudinal axis 19 of the first bone implant 2. In a first section 25 of the elongated recess 23 and at a distance X from the bottom 24 a restriction 22 is provided which restricts the area of the opening of the elongated recess 23 to a width Y orthogonal to the longitudinal axis 19 of the first bone implant 2 and at the second end 27 of the elongated recess 23. The restriction 22 forms an undercut 31 with a shoulder 21 such forming a hold for an e.g. semispherical tip 30 of a removing instrument 28 when pulling out the closing cover 7 from said through hole 11 in said first bone implant 2. In the second section 32 of the elongated recess 23 the opening of the elongated recess 23 is not restricted such allowing the shaft 29 of the removing instrument 28 to pass therethrough. The removing instrument 28 can such be inserted into the removal hole 20 in the second section 32 of the elongated hole 23 and displaced into the first section 25 for removal of the closing cover 7.

The embodiment of the bone fixation device 1 illustrated in FIG. 3 differs from the embodiment of FIGS. 1 and 2 only therein that:

A) the elongated through hole 11 is provided with a first section with a concavely rounded recess 12 suitable for receiving a hemispherical head 6 of a bone screw 33 (FIG. 1) and at the side of said first section a second section with a conical internal thread 60 at such allowing to engage a complementary conical locking screw head 61 of a bone screw 33 used as a second bone implant 5;

B) a front cover 50 is provided within the through hole 11; and

C) the socket 62, e.g. hexagon socket for receiving a screw driving instrument in the locking screw head 61 is filled with a gel before the closing cover 7 is attached to the through hole 11.

Said front cover 50 is fixed to the wall of the through hole 11 by means of an adhesive but could be fixed by means of a press fit or form fit (lip/groove) in other embodiments. The hole 63 in said front cover 50 can be produced during insertion of the second bone implant 5, i.e. the bone screw, e.g. by means of the self-drilling quality of the bone screw.

Figure 4:
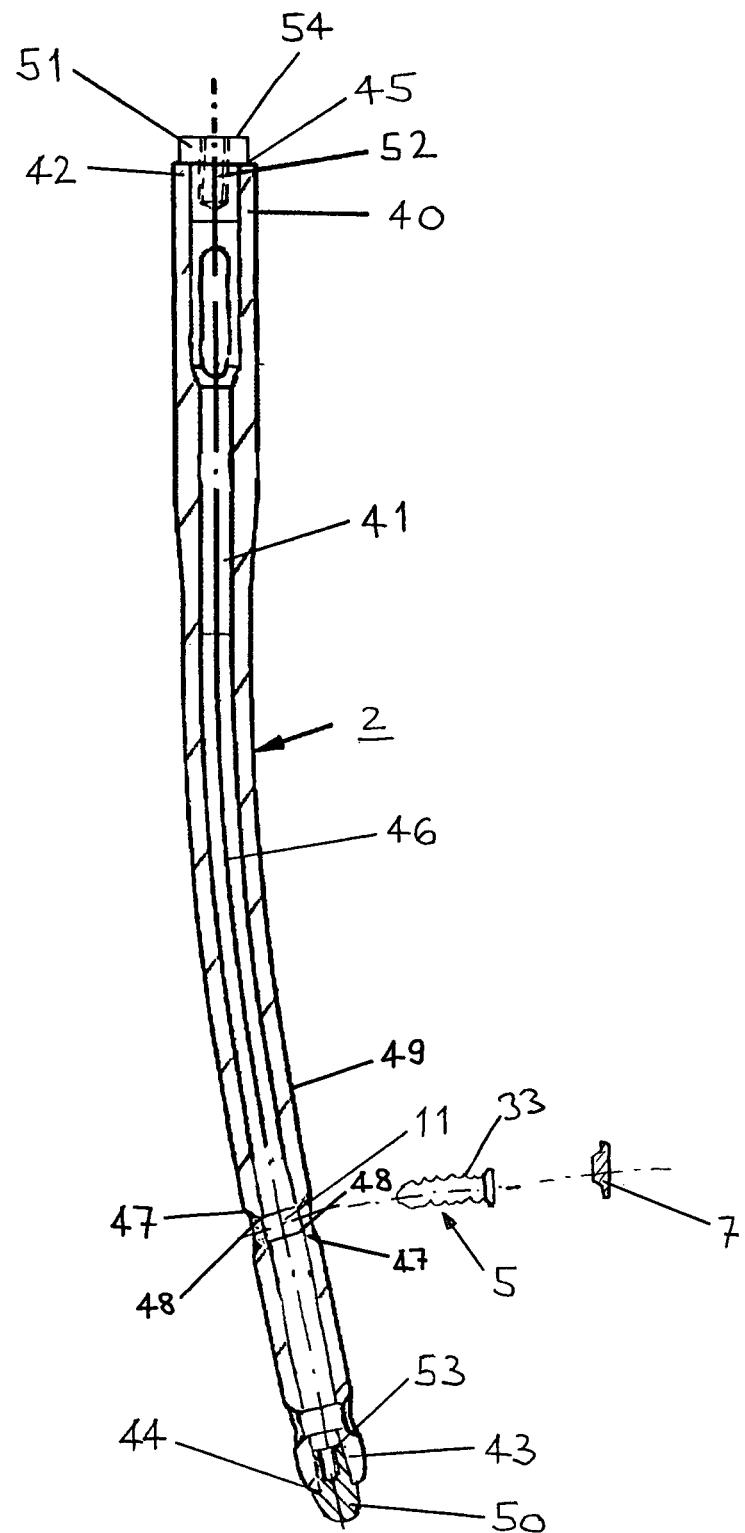
FIG. 4 illustrates a longitudinal section through a further embodiment of the bone fixation device according to the invention.

FIG. 4 illustrates an embodiment of the bone fixation device 1 with an intramedullary nail 40 as the first bone implant 2. The intramedullary nail 40 comprises a longitudinal axis 46 and a cavity 41 extending parallel to said longitudinal axis 46. In a front portion of the intramedullary nail 40 two through holes 11 suitable for receiving a locking bone screw 33 each penetrate the intramedullary nail 40 transverse to said longitudinal axis 46. In the present embodiment each the aforementioned locking bone screws 33 presents a second bone implant 5. Further, said intramedullary nail 40 comprises a rear end 42 and a front end 43 and said cavity 41 extends through said intramedullary nail 40 from said rear end 42 to said front end 43 such forming a front opening 44 and a rear opening 45. Each of said through holes 11 forms two outer openings 47 with the area A at the peripheral surface 49 of the intramedullary nail 40 and two inner openings 48 towards said cavity 41. A closing cover 7 each is used for closing said outer openings 47 of said through holes 11.

Additionally, the intramedullary nail 40 comprises a front cover 50 for closing said front opening 44 of said cavity 41. The front cover 50 can be fixed to the intramedullary nail 40 by elastically compressing said front cover 50 during insertion until a front portion of said front cover 50 protrudes over the front end 43 of the intramedullary nail 40. Once the front portion of said front cover 50 has passed the front opening 44 of the intramedullary nail 40 during insertion of the front cover 50 into the cavity 41 said front portion elastically expands such forming a shoulder towards the rear portion of the front cover 50 which contacts the front end 43 of the intramedullary nail 40. The rear portion of said front cover 50 is then fixed in the cavity 41 by means of a press fit.

In the present embodiment the intramedullary nail 40 further comprises an end cover 51 for closing said rear opening 45 of said cavity 41. Said front cover 50 and said end cover 51 each has a trailing end 53, 54 which is provided with a pocket hole 52 with an internal thread for threadably receiving an insertion instrument.

The cavity 41 of the intramedullary nail 40 can be used for placement of the intramedullary nail 40 in the correct position within the medullary channel of a bone with the use of a guide wire (not shown). The guide wire is removed after placement of the intramedullary nail 40 leaving the cavity 41 empty and open at the front end 43 and the rear end 42 of the intramedullary nail 40. The front cover 50 is suitable for closing said front opening 44 of said cavity 41 to prevent bone and soft tissue ingrowth and/or bacterial invasion into said cavity 41 from the front end 43 of the intramedullary nail 40. Said front cover 50 can be inserted by means of a special instrument or may be attached to said guide wire. The front cover 50 can then be detached from said guide wire as it interferes with said front opening 44 of said cavity 41 upon removal of said guide wire. After removal of said guide wire and closure of said front opening 44 of said cavity 41 the remainder of the cavity 41 can be filled with a gel. Finally, said end cover 51 can be attached to the rear end 42 of said intramedullary nail 40 for closure of the rear opening 45 of said cavity 41.

While one description of the present invention is described above, it should be understood that the various features can be used singly or in any combination thereof. The scope of the present invention is accordingly defined as set forth in the appended claims.

What is claimed is:

1. A bone fixation device comprising:
   a first bone implant with at least one through hole defined at least in part by a through hole wall, wherein said first bone implant comprises a hollow intramedullary nail with a longitudinal cavity, wherein said at least one through hole has two outer openings with an area A at a peripheral surface of the hollow intramedullary nail and two inner openings towards said longitudinal cavity;
   at least one second bone implant with a head and a shaft for insertion into said at least one through hole; and
   at least one closing cover for closing one of said two outer openings of said at least one through hole,
   wherein said closing cover is made of an elastic material and is removably attachable to said first bone implant;
   wherein said closing cover is dimensioned and shaped in such a way that, upon attachment to said first bone implant, the elastic material makes contact with at least a portion of the through hole wall at one of said two outer openings, and said closing cover covers at least the entire area A of one of said two outer openings and the head of said at least one second bone implant and any additional second bone implants inserted into said at least one through hole thereby preventing bacterial invasion through one of said two outer openings into said at least one through hole; and
   wherein the closing cover is removably fixable to the through hole wall at one of said two outer openings by a press-fit arrangement, a form-fit arrangement or an adhesive.

2. The bone fixation device according to claim 1, wherein said at least one closing cover is suitable for closing GF one of said two outer openings of said through hole for preventing bone and soft tissue ingrowth into said second bone implant.

3. The bone fixation device according to claim 1, wherein said second bone implant is a bone screw.

4. The bone fixation device according to claim 1 wherein said closing cover comprises a material with a contact angle smaller than 60°.

5. The bone fixation device according to claim 4, wherein said material is a hydrophilic material.

6. The bone fixation device according to claim 1, wherein said closing cover comprises a material with a contact angle larger than 80°.

7. The bone fixation device according to claim 6, wherein said material is a hydrophobic material.

8. The bone fixation device according to claim 7, wherein said material is a degradable polymer.

9. The bone fixation device according to claim 7, wherein said material is a non-degradable polymer.

10. The bone fixation device according to claim 9, wherein said material is a composite of said material and another material.

11. The bone fixation device according to claim 8, wherein said material is a composite of said material and another material.

12. The bone fixation device according to claim 1, wherein said closing cover is dimensioned and shaped in such a way that upon attachment to said bone implant it is apt to cover more than said area A to prevent tissue and bacteria ingrowth of said outer opening.

13. The bone fixation device according to claim 1, wherein the geometry of at least a central portion of said closing cover is adapted to the shape of the through hole.

14. The bone fixation device according to claim 1, wherein the geometry of the lower side of the said closing cover is adapted to the shape of said head of said second bone implant.

15. The bone fixation device according to claim 1, wherein said closing cover is dimensioned and shaped in such a way that upon attachment to said first bone implant it covers more than one of said through holes.

16. A kit for bone fixation comprising:
    a bone fixation device according to claim 1; and
    a gel suitable to provide a hydrophobic or hydrophilic surface and which is non-degradable by the surrounding body fluids for filling residual cavities in said first and/or second bone implant to prevent bone ingrowth and/or to prevent- bacteria from filling said residual cavities.

17. The kit for bone fixation according to claim 16, wherein said gel is a highly hydrated polymeric material with a water content >30% by weight.

18. The kit for bone fixation according to claim 17, wherein said gel is an injectable solution that forms said gel in-situ.

19. The kit for bone fixation according to claim 16, wherein said gel is based on a polymer with hydrophilic chains of synthetic origin.

20. The kit for bone fixation according to claim 16, wherein said gel is based on a polymer with hydrophilic chains of natural origin.

21. The bone fixation device according to claim 1, wherein the closing cover is made entirely of the elastic material.

22. A bone fixation device comprising:
    a bone implant with at least one through hole defined at least in part by a through hole wall, wherein said first bone implant comprises a hollow intramedullary nail with a longitudinal cavity, wherein said at least one through hole has two outer openings with an area A at a peripheral surface of the hollow intramedullary nail and two inner openings towards said longitudinal cavity;

at least one closing cover for closing one of said two outer openings of said through hole for preventing bone and soft tissue ingrowth and/or bacterial invasion into said through hole, wherein said closing cover is removably attachable to said bone implant; and wherein said closing cover is dimensioned and shaped in such a way that, upon attachment to said bone implant, the closing cover makes contact with at least a portion of the through hole wall at one of said two outer openings, and said closing cover also covers said area A of said area A of one of said two outer openings and some of the peripheral surface surrounding said one of said two outer openings thereby preventing bacterial invasion through one of said two outer openings into said at least one through hole.

23. The bone fixation device according to claim 22, wherein said bone fixation device comprises a second bone implant.

24. The bone fixation device according to claim 22, wherein the closing cover is unitary.

25. A bone fixation device comprising:

a first bone implant with at least one through hole, wherein said first bone implant is a hollow intramedullary nail with a longitudinal axis and a longitudinal cavity extending parallel to said longitudinal axis, wherein said at least one through hole has two outer openings with an area A at a peripheral surface of the hollow intramedullary nail and two inner openings towards said longitudinal cavity, and wherein said at least one through hole penetrates said intramedullary nail transverse to said longitudinal axis at said two outer openings at the peripheral surface of the intramedullary nail and at said two inner openings towards said cavity;

at least one second bone implant with a head and a shaft for insertion into said at least one through hole; and at least one closing cover for closing said one of said two outer openings of said at least one through hole for preventing bone and soft tissue ingrowth and/or bacterial invasion into said at least one through hole, wherein said closing cover is removably attachable to said first bone implant;

wherein said closing cover is dimensioned and shaped in such a way that upon attachment to said first bone implant it covers at least the entire area A of one of said two outer openings and the head of said at least one second bone implant and any additional second bone implants inserted into said through hole; and wherein said closing cover is made of an elastic material.

26. The bone fixation device according to claim 25, wherein said intramedullary nail comprises a rear end and a front end and wherein said cavity extends through said intramedullary nail from said rear end to said front end such forming a front opening and a rear opening.

27. he bone fixation device according to claim 26, wherein said bone fixation device additionally comprises a front cover for closing said front opening of said cavity in the case of an intramedullary nail as the first bone implant.

28. The bone fixation device according to claim 26, wherein said bone fixation device additionally comprises an end cover for closing said rear opening of said cavity in the case of an intramedullary nail as the first bone implant.

* * * * *